United States Patent
Choi et al.

(10) Patent No.: US 11,581,518 B2
(45) Date of Patent: Feb. 14, 2023

(54) PROBE INTEGRATED WITH ORGANIC LIGHT SOURCE AND MANUFACTURING METHOD THEREOF

(71) Applicant: KOREA ADVANCED INSTITUTE OF SCIENCE AND TECHNOLOGY, Daejeon (KR)

(72) Inventors: KyungCheol Choi, Daejeon (KR); Hyunjoo Lee, Daejeon (KR); MiKyung Kim, Daejeon (KR); Somin Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 99 days.

(21) Appl. No.: 17/025,395

(22) Filed: Sep. 18, 2020

(65) Prior Publication Data

US 2021/0091344 A1  Mar. 25, 2021

(30) Foreign Application Priority Data

Sep. 19, 2019 (KR) .................. 10-2019-0115599

(51) Int. Cl.
*H01L 51/00* (2006.01)
*A61B 5/262* (2021.01)
(Continued)

(52) U.S. Cl.
CPC .......... *H01L 51/56* (2013.01); *H01L 51/001* (2013.01); *H01L 51/0023* (2013.01); *H01L 51/5253* (2013.01); *A61B 5/0084* (2013.01)

(58) Field of Classification Search
CPC . H01L 27/3225; H01L 51/5203; H01L 51/52; A61N 5/0622; A61B 5/262; G01Q 60/38; G01R 1/071
See application file for complete search history.

(56) References Cited

U.S. PATENT DOCUMENTS

| 10,188,304 B2 | 1/2019 | Jamieson et al. |
| 2008/0071313 A1* | 3/2008 | Stevenson ............ A61N 1/3752 607/2 |

(Continued)

FOREIGN PATENT DOCUMENTS

| KR | 20060123810 A | 12/2006 | |
| KR | 20070059877 | * 6/2007 | ......... H01L 51/0016 |

(Continued)

OTHER PUBLICATIONS

Lee, So-Min; "Fabrication of μ-OLEDs on Neural Probe" thesis submitted to the faculty of Korea Advanced Institute of Science and Technology; Dec. 5, 2018.

*Primary Examiner* — Caridad Everhart
(74) *Attorney, Agent, or Firm* — Kolitch Romano Dascenzo Gates LLC

(57) ABSTRACT

Disclosed are a probe integrated with an organic light source and a manufacturing method thereof. An organic light source integration method includes forming a first thin film encapsulation layer on a probe shank, depositing a first electrode in a first region on the first thin film encapsulation layer, depositing an insulating layer in a second region on the first thin film encapsulation layer, depositing a light emitting layer on the first electrode and the insulating layer, depositing a second electrode on the light emitting layer, and forming a second thin film encapsulation layer on the second electrode.

11 Claims, 15 Drawing Sheets

(51) Int. Cl.
*G01Q 60/38* (2010.01)
*H01L 51/56* (2006.01)
*H01L 51/52* (2006.01)
*A61B 5/00* (2006.01)

(56) References Cited

U.S. PATENT DOCUMENTS

| | | | |
|---|---|---|---|
| 2009/0134025 A1 | 5/2009 | Shtein et al. | |
| 2009/0299167 A1* | 12/2009 | Seymour | A61B 5/24 600/372 |
| 2012/0074433 A1* | 3/2012 | Zhao | H01L 51/0024 257/E33.056 |
| 2018/0154152 A1* | 6/2018 | Chabrol | A61N 1/0534 |
| 2018/0193663 A1 | 7/2018 | Deligianni et al. | |

FOREIGN PATENT DOCUMENTS

| | | |
|---|---|---|
| KR | 20070059877 A | 6/2007 |
| KR | 20110036569 A | 4/2011 |
| KR | 20170039673 A | 4/2017 |
| WO | 2011068696 A2 | 6/2011 |

\* cited by examiner

L322 (50 μm x 50 μm) voltage driving OM image @ 4V-8V

L324 (10 μm x 10 μm) voltage driving OM image @ 3V~8V

PROBE INTEGRATED WITH ORGANIC LIGHT SOURCE AND MANUFACTURING METHOD THEREOF

CROSS-REFERENCES

The following application is incorporated herein, in its entirety, for all purposes: Korean Patent Application No. 10-2019-0115599, filed on Sep. 19, 2019, in the Korean Intellectual Property Office.

INTRODUCTION

A probe may be connected to a sensor using a needle-shaped tool made of metal as a kind of electrode to measure the temperature of a material, vibration, electrical changes during a chemical change, and the like. An optogenetic probe may measure electrical changes occurring at neurons, at the same time stimulating neurons expressing photoproteins with light by integrating a light source and a neural signal measuring electrode into the probe.

An existing optogenetic probe induces a laser beam to the end of a brain insertion part of the optogenetic probe by integrating a micro-light-emitting diode (pLED) within the device, or using a waveguide, thereby irradiating light onto tissues. However, the heat generated locally in the LED may incidentally activate and damage neurons. The waveguide also has a great light loss and thus, has low power efficiency.

An organic light-emitting diode (OLED) is a thin film LED made of a film of an organic compound, where a light-emitting layer emits light through electron-hole recombination.

SUMMARY

An aspect of the present disclosure provides a method of integrating an organic light source on a probe and a method of finely patterning a thin film encapsulation layer to protect an organic light source.

According to an aspect of the present disclosure, there is provided a method of integrating an organic light source, the method including forming a first thin film encapsulation layer on a probe shank, depositing a first electrode in a first region on the first thin film encapsulation layer, depositing an insulating layer in a second region on the first thin film encapsulation layer, depositing a light emitting layer on the first electrode and the insulating layer, depositing a second electrode on the light emitting layer, and forming a second thin film encapsulation layer on the second electrode.

The light emitting layer may include an organic light emitting material.

The depositing of the first electrode may include forming a fine pattern on the first thin film encapsulation layer using a photoresist, depositing a metal layer on the fine pattern, and forming the first electrode in the first region by performing lift-off on the metal layer.

The forming of the fine pattern may include patterning a region using the photoresist, except for a region for the first electrode and a region in which the first electrode is to be coupled to a power supply.

The depositing of the insulating layer may include depositing the insulating layer only in the second region so that only a region for the first electrode is opened on the first thin film encapsulation layer.

The depositing of the light emitting layer may include depositing the light emitting layer in high vacuum using a thermal evaporator.

The depositing of the light emitting layer may include depositing the light emitting layer only on the first electrode without covering a contact line of the second electrode.

The forming of the first thin film encapsulation layer may include patterning a photoresist in a region on a wafer except for the probe shank to form the first thin film encapsulation layer on the probe shank, coating the entire surface of the wafer with a thin film encapsulation layer, and forming the first thin film encapsulation layer by performing lift-off on the thin film encapsulation layer.

The forming of the second thin film encapsulation layer may include patterning a photoresist in a region on a wafer except for the probe shank to form the second thin film encapsulation layer on the second electrode, coating the entire surface of the wafer with a thin film encapsulation layer, and forming the second thin film encapsulation layer by performing lift-off on the thin film encapsulation layer.

The coating of the entire surface of the wafer with the thin film encapsulation layer may include coating the entire surface of the wafer with the thin film encapsulation layer through atomic layer deposition (ALD) and spin coating.

The method may further include depositing a sacrificial layer on a wafer, and manufacturing the probe shank on the sacrificial layer.

The probe shank may include a signaling electrode.

According to another aspect, there is provided a probe integrated with an organic light source, the probe including a probe shank, a first thin film encapsulation layer formed on the probe shank, a first electrode deposited in a first region on the first thin film encapsulation layer, an insulating layer deposited in a second region on the first thin film encapsulation layer, a light emitting layer deposited on the first electrode and the insulating layer, a second electrode deposited on the light emitting layer, and a second thin film encapsulation layer formed on the second electrode.

The light emitting layer may include an organic light emitting material.

The probe shank may include a signaling electrode.

The second region may include all regions except for the first region on the first thin film encapsulation layer.

The light emitting layer may be deposited only on the first electrode without covering a contact line of the second electrode.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages will become apparent and more readily appreciated from the following description of example embodiments, taken in conjunction with the accompanying drawings, of which.

DETAILED DESCRIPTION

Figure 1:
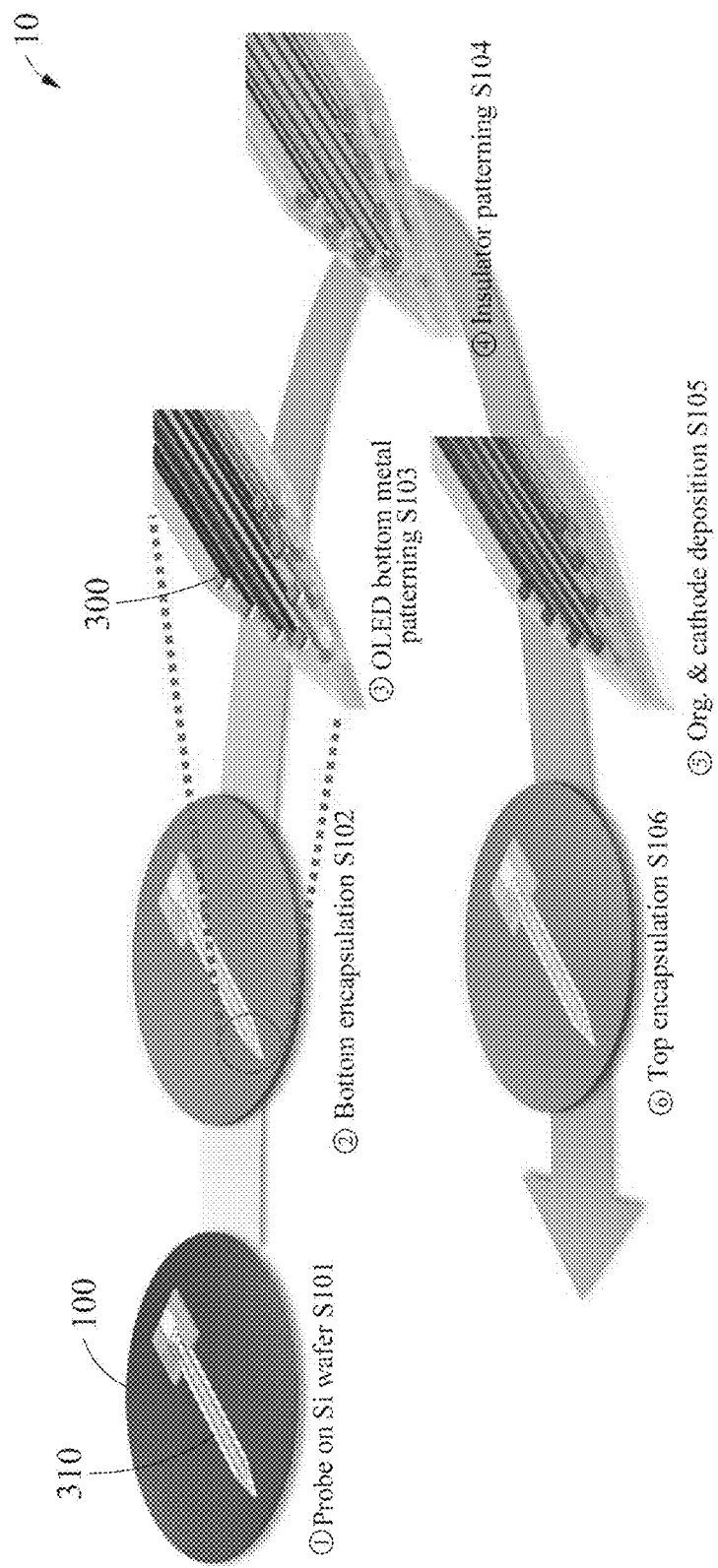
FIG. 1 illustrates a process of an organic light source integration method according to an example embodiment.

Hereinafter, example embodiments will be described in detail with reference to the accompanying drawings. However, various alterations and modifications may be made to the example embodiments. Here, the example embodiments are not construed as limited to the disclosure. The example embodiments should be understood to include all changes, equivalents, and replacements within the idea and the technical scope of the disclosure.

The terminology used herein is for the purpose of describing particular example embodiments only and is not to be limiting of the example embodiments. The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Terms, such as first, second, and the like, may be used herein to describe components. Each of these terminologies is not used to define an essence, order or sequence of a corresponding component but used merely to distinguish the corresponding component from other component(s). For example, a first component may be referred to as a second component, and similarly the second component may also be referred to as the first component.

Unless otherwise defined, all terms including technical and scientific terms used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the example embodiments with reference to the accompanying drawings, like reference numerals refer to like constituent elements and a repeated description related thereto will be omitted. In the description of example embodiments, detailed description of well-known related structures or functions will be omitted when it is deemed that such description will cause ambiguous interpretation of the present disclosure.

FIG. 1 illustrates a process of an organic light source integration method according to an example embodiment.

An organic light source may be integrated on a probe 200. For example, the organic light source may be finely patterned and integrated on a flexible probe 200 including a signaling electrode.

A thin film encapsulation layer may be formed to protect the probe 200 from an external environment. For example, the thin film encapsulation layer may be formed on the bottom and/or on the top of the organic light source integrated in the probe 200 to protect the organic light source from the external environment.

If an organic light source is manufactured using only a shadow mask, delicate patterning may not be performed at pattern edges due to the characteristics of shadow mask process, such that the brightness and/or color of the light source may be nonuniform. In addition, since the shadow mask needs to be changed in situ in a high-vacuum chamber, misalignment may occur at this time. If the length resolution of the pattern is reduced to a few micrometers (μm) through shadow mask process, the accuracy of the pattern may decrease.

Further, since there exists a space between a substrate and a mask due to the thickness of the shadow mask during deposition using the shadow mask, the size of the manufactured organic light source may be larger than 900 μm$^2$. That is, if an organic light source is manufactured with a multi-layer structure of a metal electrode layer, an organic light source layer, and the like, it may be difficult to accurately adjust the organic light source to a desired size.

The light source integrated into the probe 200 may be manufactured in a smaller size than the conventional light source, and a thin film encapsulation layer is formed to protect the light source from the external environment when inserted into the body. Thus, the probe 200 may stably and selectively stimulate neurons in a local site, thereby enabling accurate brain research.

By fine patterning instead of the process method using a shadow mask, the organic light source may be manufactured in a size sufficient to stimulate neurons, for example, in a size of 10 μm×10 μm, and may further be manufactured with a length of at least several μm. In addition, since a 4-inch wafer process is possible, a large area process may be performed.

For example, an organic light source of a size of tens to hundreds of μm$^2$ may be integrated in the probe 200, and a thin film encapsulation layer of the organic light source may be finely patterned to protect the organic light source from the outside.

A micro-organic light-emitting diode (OLED) and a signaling electrode may be integrated into an optogenetic brain probe 200. For example, on the flexible and transparent brain probe 200, an organic light source (for example, an OLED) with a small local heat production may be manufactured and integrated in a micro size, and a thin film encapsulation layer capable of protecting the integrated micro OLED may be finely patterned, such that the light source may be protected.

A micro-OLED is a light source that has not been used in the conventional implantable photic stimulation brain probes. The brain probe 200 integrated with the micro OLED and the signaling electrode for measuring signals of neurons together may enable stable and local photic stimulation and measurement of neuron signals at the same time.

Hereinafter, a process of an organic light source integration method 10 will be described.

In operation S101, the organic light source integration method 10 may dispose a probe shank 310 on a wafer 100. For example, the probe shank 310 may be disposed on the wafer 100 to integrate an organic light source on the probe shank 310.

In operation S102, the organic light source integration method 10 may form a bottom thin film encapsulation layer on the probe shank 310. For example, the organic light source integration method 10 may form the bottom thin film encapsulation layer by patterning a thin film encapsulation layer on the probe shank 310 through thin film encapsulation.

In operation S103, the organic light source integration method 10 may pattern an anode on the bottom thin film encapsulation layer. For example, the anode may be an OLED anode.

In operation S104, the organic light source integration method 10 may pattern an insulator on the bottom thin film encapsulation layer. For example, the organic light source integration method 10 may deposit an insulating layer by patterning the insulator in a region where the anode is not formed on the bottom thin film encapsulation layer.

In operation S105, the organic light source integration method 10 may deposit a light emitting layer and a cathode on the anode and the insulating layer. For example, the organic light source integration method 10 may deposit the light emitting layer on the anode and the insulating layer, and deposit the cathode on the light emitting layer. The light emitting layer may include an organic light emitting material.

After the cathode is deposited, the organic light source integration method 10 may form a top thin film encapsulation layer, in operation S106. For example, the organic light source integration method 10 may pattern a thin film encapsulation layer through thin film encapsulation to protect the organic light emitting layer. That is, the top thin film encapsulation layer may be formed to enclose the anode, the insulating layer, the light emitting layer, and the cathode deposited on the bottom thin film encapsulation layer.

Figure 2:
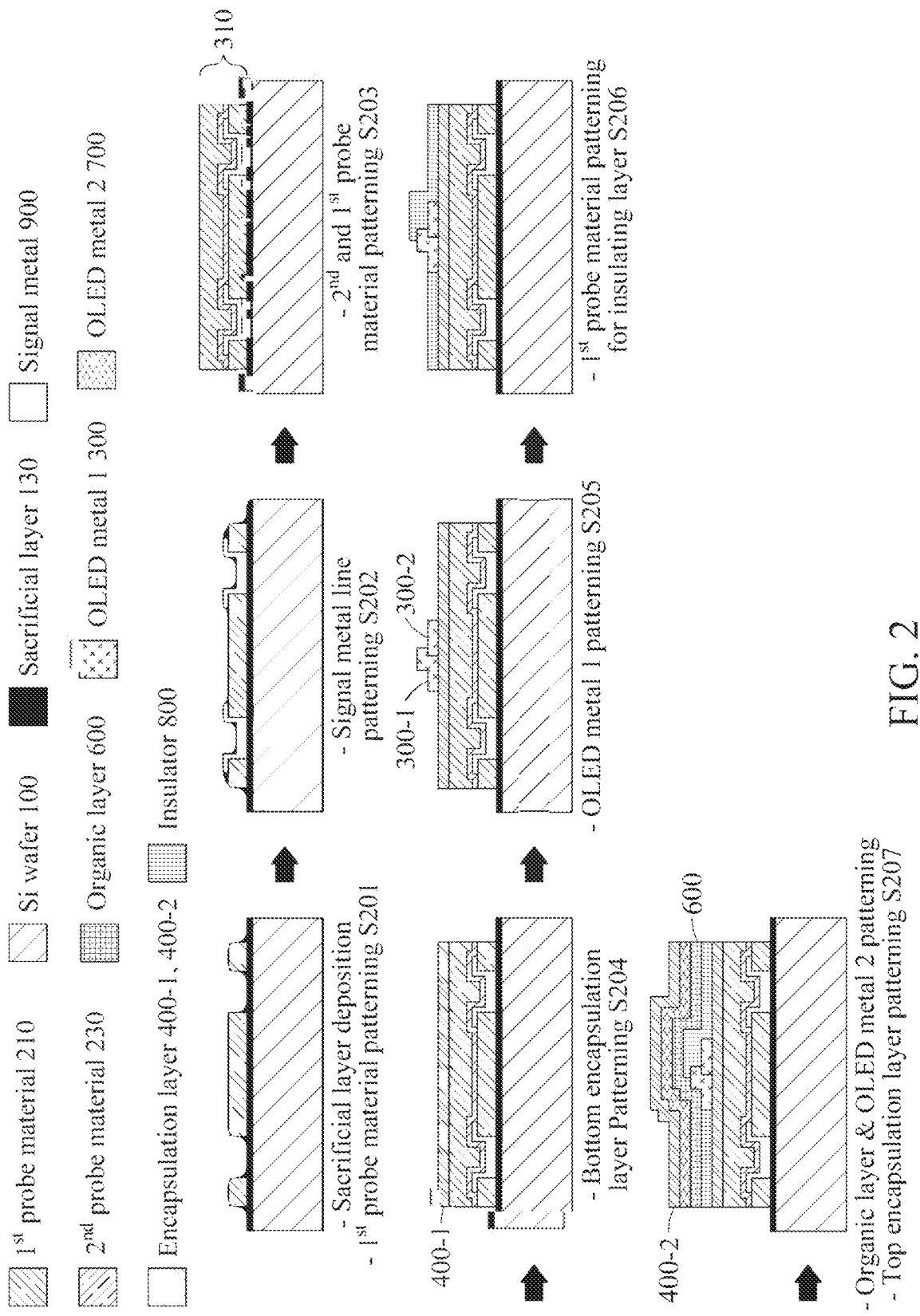
FIG. 2 illustrates a detailed process of the organic light source integration method shown in FIG. 1.

FIG. 2 illustrates a detailed process of the organic light source integration method shown in FIG. 1.

The organic light source integration method 10 may deposit, on the probe shank 310 of the brain probe 200, thin film encapsulation layers 400-1 and 400-2, a first OLED metal 300, a second OLED metal 700, a light emitting layer 600, and an insulating layer 800.

In this case, the first OLED metal 300 may include an anode 300-1 and contact line 300-2, and the second OLED metal 700 may be a cathode layer, and a first probe material 210 may be used for the insulating layer 800. In addition, the light emitting layer 600 may be an organic layer.

A process of manufacturing a probe may include operations S201 to S203 which will be described in detail below with reference to FIG. 7.

In operation S204, the bottom thin film encapsulation layer 400-1 may be formed on the probe shank 310. The bottom thin film encapsulation layer 400-1 may be formed on the entire upper surface of the probe shank 310. For example, the upper surface of the probe shank 310 may be coated with the bottom thin film encapsulation layer 400-1 to protect the organic light source.

Fine patterning for the first OLED metal 300 may be performed on the bottom thin film encapsulation layer 400-1. A photoresist (not shown) may be formed on the bottom thin film encapsulation layer 400-1, and a fine pattern for the first OLED metal 300 may be formed on the bottom thin film encapsulation layer 400-1 through the photoresist (not shown). In this case, the photoresist (not shown) may be formed in a region except for a region (for example, a first region) on the bottom thin film encapsulation layer 400-1 in which the first OLED metal 300 is to be disposed. For example, the first region may include a region for the anode 300-1 and the contact line 300-2 for connection between the anode 300-1 and a power supply (not shown) for light emission of the light source.

In operation S205, the first OLED metal 300 may be deposited along the fine pattern formed on the bottom thin film encapsulation layer 400-1. For example, the anode 300-1 and the contact line 300-2 may be deposited on the fine pattern formed on the bottom thin film encapsulation layer 400-1 using a thermal evaporator. That is, the first OLED metal 300 may be deposited on the first region on the bottom thin film encapsulation layer 400-1 in which the anode 300-1 and the contact line 300-2 are to be formed and the entire region coated with a photoresist 500.

The anode 300-1 and contact line 300-2 may be formed in the first region on the bottom thin film encapsulation layer 400-1 by performing lift-off on the first OLED metal 300. For example, the patterned photoresist (not shown) may be lifted off using an acetone solution. If the photoresist (not shown) is lifted off, the anode 300-1 and the contact line 300-2 may be formed only in the first region on the bottom thin film encapsulation layer 400-1. Through this, the anode 300-1 and the contact line 300-2 may be deposited in a region that may effectively contribute to the light emitting area.

The anode 300-1 and the contact line 300-2 can each be deposited through separate lift-off processes. For example, contact line 300-2 may be deposited first and anode 300-1 may be deposited later.

The light emitting area of the micro-sized OLED may be determined according to the size and shape of the anode 300-1 that is finely patterned (or formed by fine patterning).

A shadow mask may be used to deposit a metal layer only in the region for connection between the anode 300-1 and the power supply for light emission of the light source, on the probe shank 310. However, in this case, the size of the manufactured light source may be 900 $\mu m^2$ or more. Thus, it may be difficult to locally stimulate neurons.

In operation S206, the insulating layer 800 may be finely patterned on the bottom thin film encapsulation layer 400-1. The insulating layer 800 may be deposited in a region on the bottom thin film encapsulation layer 400-1 except for the region in which only anode 300-1 is deposited. For example, the insulating layer 800 may be deposited in a region where contact line 300-2 is deposited under the anode 300-1.

The insulating layer 800 may be finely patterned using a shadow mask and/or a photoresist (not shown). Further, the insulating layer 800 may be finely patterned and deposited by various methods such as using a thermal evaporator depending on the type of insulator that is used.

By depositing the insulating layer 800 on a region in which the anode 300-1 is not deposited on the bottom thin film encapsulation layer 400-1, misalignment between the anode 300-1 and the light emitting layer 600 may be prevented, and light may be emitted from a desired region of the light source.

That is, even when a multilayer structure is formed through fine patterning of the insulating layer 800, a micro-sized OLED may be formed on the probe shank 310 without inter-layer misalignment.

In operation S207, the light emitting layer 600 may be deposited on the anode 300-1 and the insulating layer 800. For example, the light emitting layer 600 may be deposited in high vacuum using a thermal evaporator. In this case, the light emitting layer 600 may include an organic material (for example, an organic light emitting material).

When the light emitting layer 600 is deposited using a shadow mask, the light emitting layer 600 may be deposited only on the anode 300-1 without covering a contact line 300-2.

In operation S207, the cathode layer 700 may be deposited on the light emitting layer 600. For example, the cathode layer 700 may be deposited to cover both the light emitting layer 600 and the contact line for cathode, thereby enabling passivation of the light emitting layer 600 and contact of the cathode electrode at the same time. The cathode layer 700 may be a metal layer.

In operation S207, the top thin film encapsulation layer 400-2 may be formed on the very top of the deposited organic light source. For example, top thin film encapsulation layer 400-2 may protect the organic light source by coated on the very top of the deposited organic light source.

Figure 3:
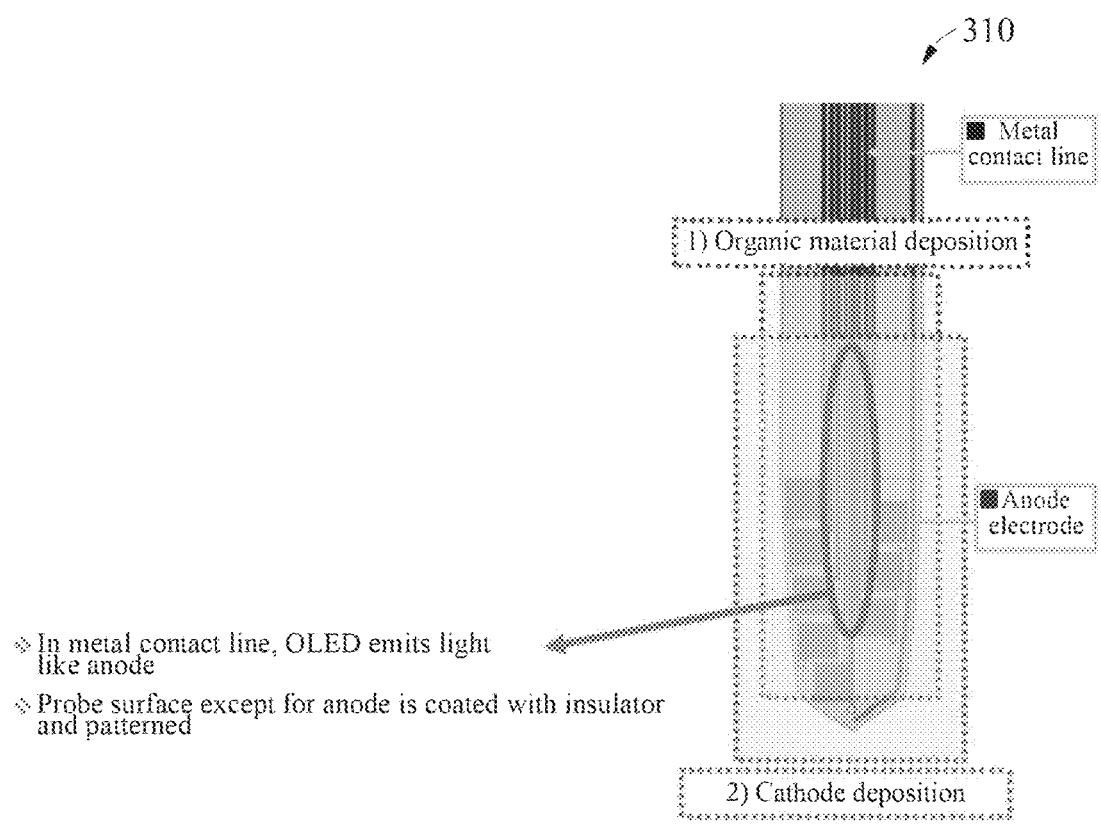
FIG. 3 illustrates a probe shank manufactured by the organic light source integration method shown in FIG. 1.

FIG. 3 illustrates a probe shank manufactured by the organic light source integration method shown in FIG. 1.

The brain probe 200 may include the probe shank 310, a neural signaling line contact pad (not shown; hereinafter, referred to as the "neural contact pad"), and an OLED cathode and anode contact line contact pad (not shown; hereinafter, referred to as the "OLED contact pad").

The first OLED metal 300, the organic material 600, and the cathode 700 may be deposited on the probe shank 310.

Power may be supplied to the anode 300-1 from the OLED contact pad (not shown) through a metal contact line 300-2, and as the power is supplied, the organic material 600 in contact with the region in which the anode 300-1 is deposited may emit light. The organic material 600 may also emit light on a metal contact line.

The probe shank 310 may include a signaling electrode. Signals of neurons may be detected through the signaling electrode, and the detected signals may be transmitted to the neural contact pad (not shown).

The surface of the probe shank 310 except for the anode 300-1 may be coated (or patterned) with an insulator, such that the anode 300-1 may stably contact the organic material 600, and the organic material 600 may emit light only at a desired site.

Figure 4A:
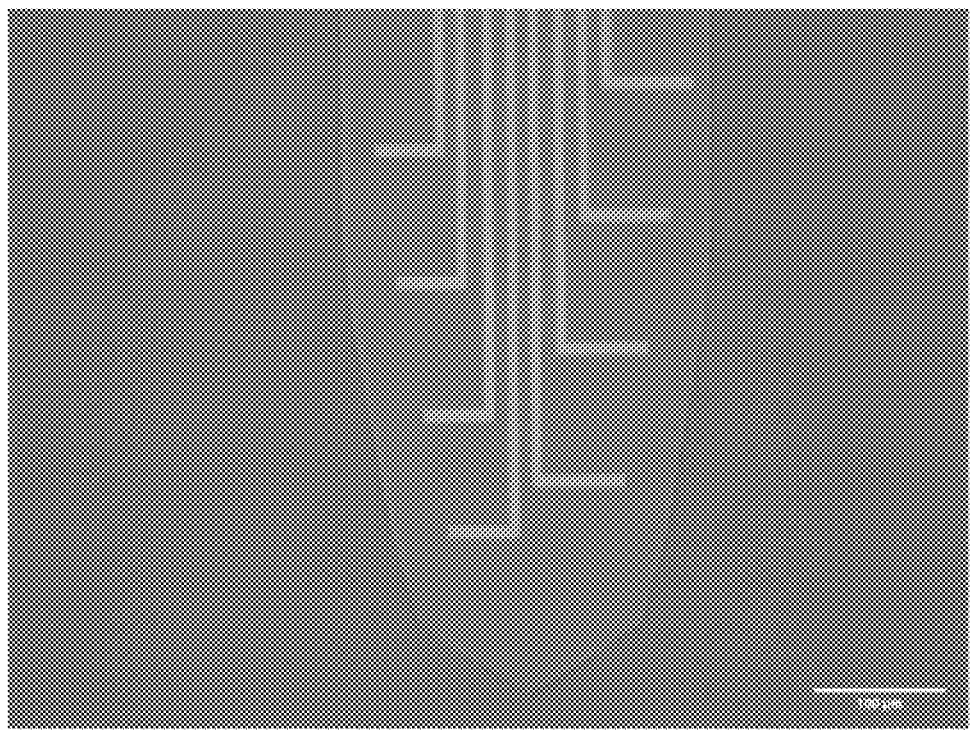
FIG. 4A illustrates a first OLED metal and insulator finely patterned in an example of a brain probe integrated with an organic light source.
Figure 4B:
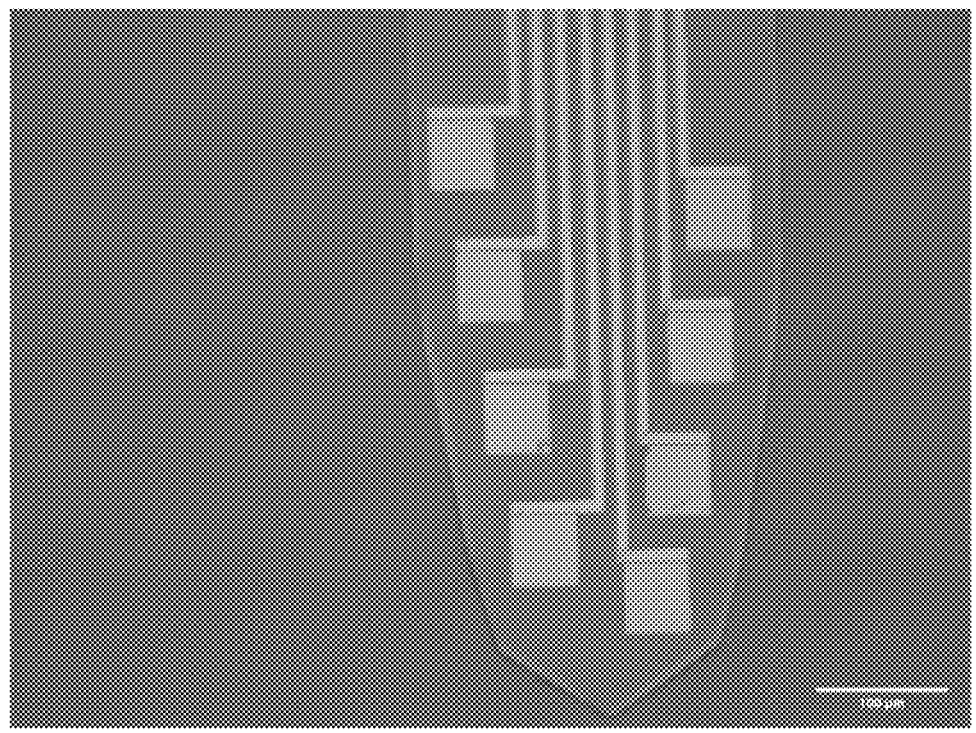
FIG. 4B illustrates a first OLED metal and insulator finely patterned in another example of a brain probe integrated with an organic light source.
Figure 4C:
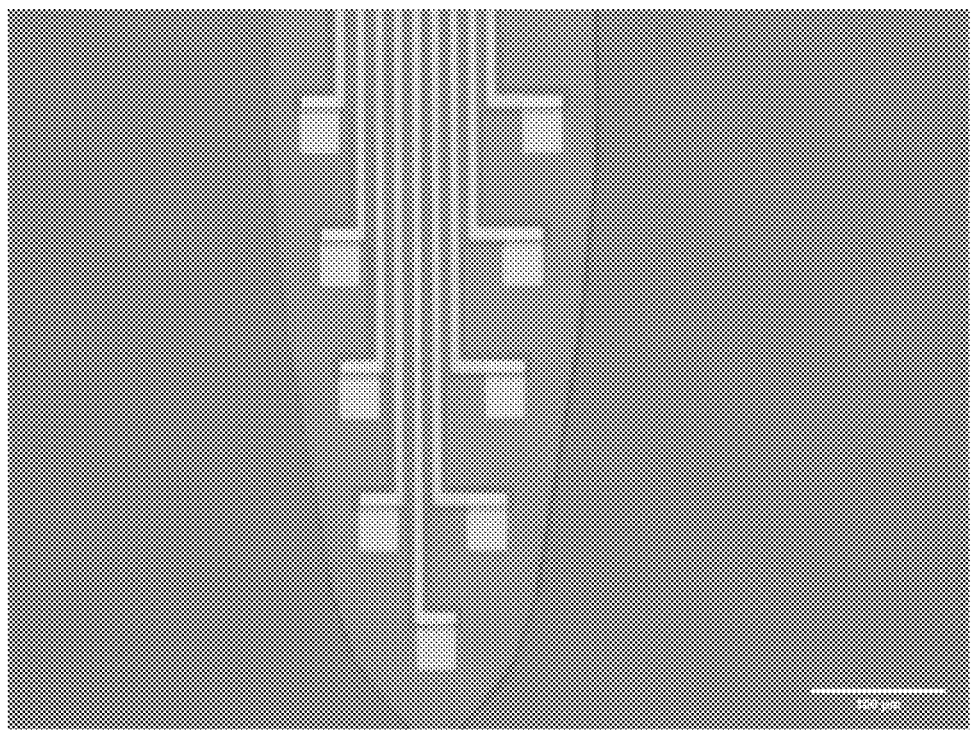
FIG. 4C illustrates a first OLED metal and insulator finely patterned in yet another example of a brain probe integrated with an organic light source.

FIGS. 4A to 4C illustrate a first OLED metal and insulator finely patterned in a brain probe integrated with an organic light source.

FIG. 4A shows an example in which the contact line 300-2 is finely patterned in a desired region on the probe shank 310.

FIG. 4B shows an example in which the anode 300-1 is finely patterned in a desired region on the probe shank 310.

FIG. 4C shows an example in which the insulator 800 is finely patterned in a desired region on the probe shank 310. The insulator 800 may be deposited except for a region where anode 300-1 is patterned. That is, insulator 800 may cover the contact line 300-2.

Figure 5:
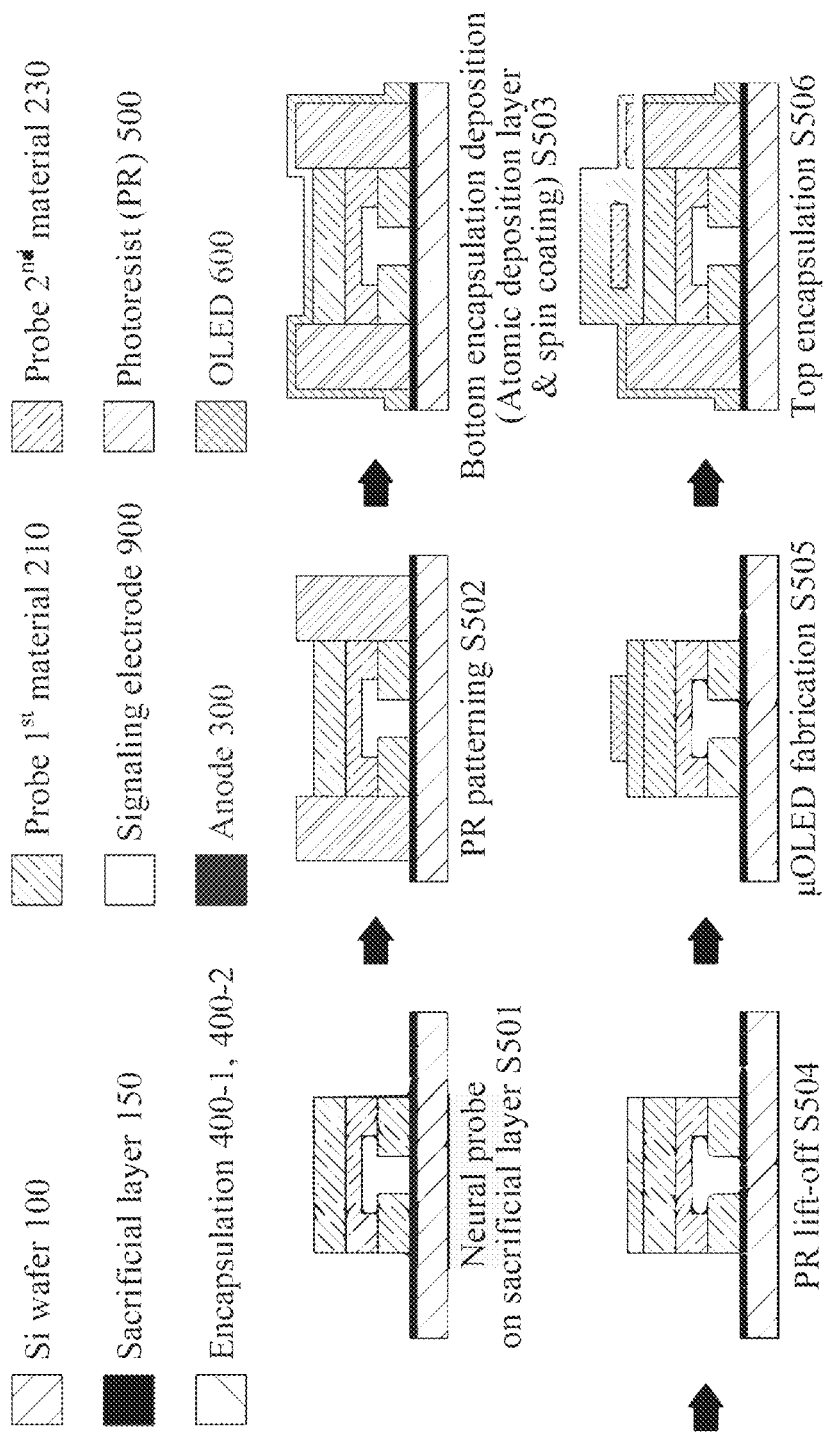
FIG. 5 illustrates a detailed process of thin film encapsulation layer formation in the organic light source integration method shown in FIG. 1.

FIG. 5 illustrates a detailed process of thin film encapsulation layer formation in the organic light source integration method shown in FIG. 1.

The thin film encapsulation layers 400-1 and 400-2 may be formed to enclose the light emitting layer 600, for example, a micro-OLED. The thin film encapsulation layers 400-1 and 400-2 may protect the micro-OLED from the external environment.

The thin film encapsulation layers 400-1 and 400-2 may be formed on the entire surface of the wafer by atomic layer deposition (ALD) and spin coating. Spin coating is a physical method of uniformly coating the entire surface with a solution, and thus it is difficult to pattern the thin film encapsulation layers 400-1 and 400-2 in a micro size. In addition, the thin film encapsulation layers 400-1 and 400-2 include organic and inorganic materials. Thus, when the thin film encapsulation layers 400-1 and 400-2 are immersed in a metal etchant such as an acid or alkaline etchant, the encapsulation layers may be damaged by the etchant and thus, hardly maintain their original functions.

The entire surface of the wafer may be coated with the thin film encapsulation layers 400-1 and 400-2, and then the thin film encapsulation layers 400-1 and 400-2 may be finely patterned using lift-off.

That is, the thin film encapsulation layers 400-1 and 400-2 that cannot be finely patterned may be finely patterned, by adjusting the hard bake time of the photoresist 500 to form the fine pattern of the thin film encapsulation layers 400-1 and 400-2.

The organic and inorganic layers formed on the entire surface of the wafer 100 may be finely patterned through spin coating and ALD by controlling the hard bake time. Thus, the micro-sized organic light source 600 having stable performance may be integrated into the micro-brain probe 200.

In operation S501, the probe shank 310 may be disposed on a sacrificial layer 150.

In operation S502, the photoresist 500 may be patterned to enclose the perimeter of the probe shank 310. The entire surface of the wafer, except for the region in which the probe shank 310 is disposed, may be coated with the photoresist 500. Accordingly, if the photoresist 500 is lifted off, the bottom thin film encapsulation layer 400-1 may be formed only on the probe shank 310.

In operation S503, the thin film encapsulation layer 400-1 may be formed on the entire surface of the wafer by ALD and spin coating.

The bottom thin film encapsulation layer 400-1 may be formed on the probe shank 310 by lifting off the photoresist 500. If the photoresist 500 is lifted off, the thin film encapsulation layer 400-1 on the region coated with the photoresist 500 may be removed, and only the thin film encapsulation layer 400-1 on the probe shank 310 not coated with the photoresist 500 may be retained, whereby the bottom thin film encapsulation layer 400-1 may be formed on the probe shank 310.

A micro-OLED may be manufactured on the bottom thin film encapsulation layer 400-1. For example, the micro-OLED may be manufactured by depositing the anode 300, the insulating layer 800, the light emitting layer 600, and the cathode 700 on the bottom thin film encapsulation layer 400-1.

The thin film encapsulation layer 400-2 may be formed on the top to enclose the micro-OLED disposed on the probe shank 310. As in the process of forming the bottom thin film encapsulation layer 400-1, the photoresist 500 may be patterned in the perimeter of the probe shank 310, and the entire surface of the wafer may be coated with the thin film encapsulation layer 400-2, in operation S506.

The top thin film encapsulation layer 400-2 enclosing the micro-OLED may be formed by lifting off the photoresist 500.

The bottom thin film encapsulation layer 400-1 and the top thin film encapsulation layer 400-2 may completely enclose the micro-OLED disposed on the probe shank 310, thereby protecting the micro-OLED from the external environment.

Figure 6A:
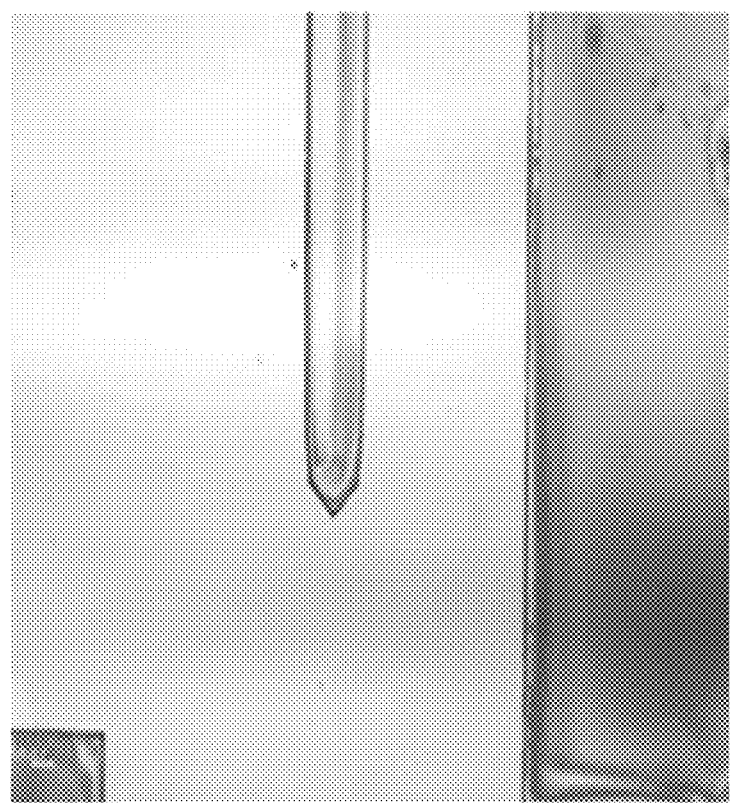
FIG. 6A illustrates a thin film encapsulation layer of a probe manufactured through the thin film encapsulation layer formation shown in FIG. 5.
Figure 6B:
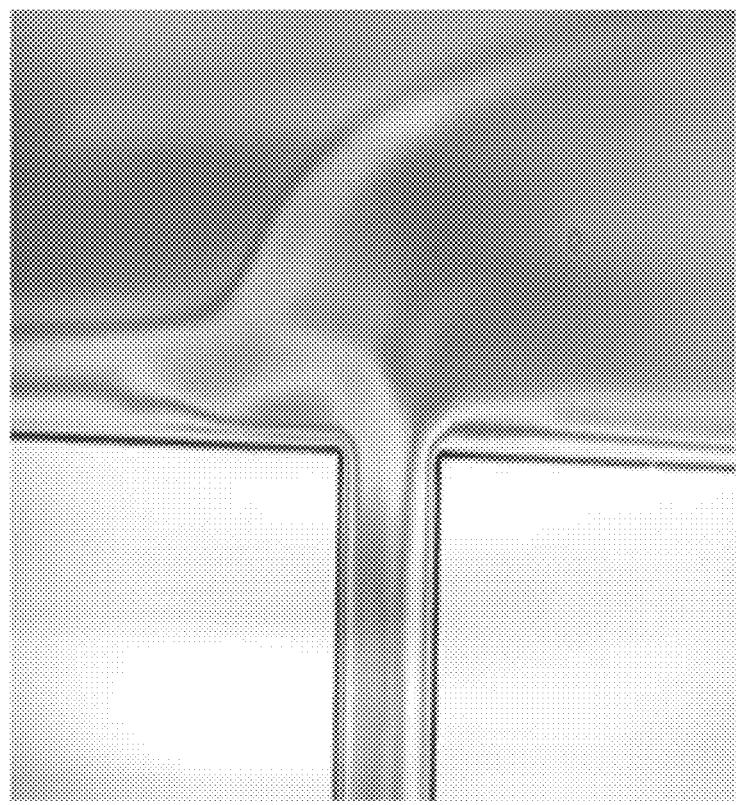
FIG. 6B illustrates a portion of the probe shown in FIG. 6A.
Figure 6C:
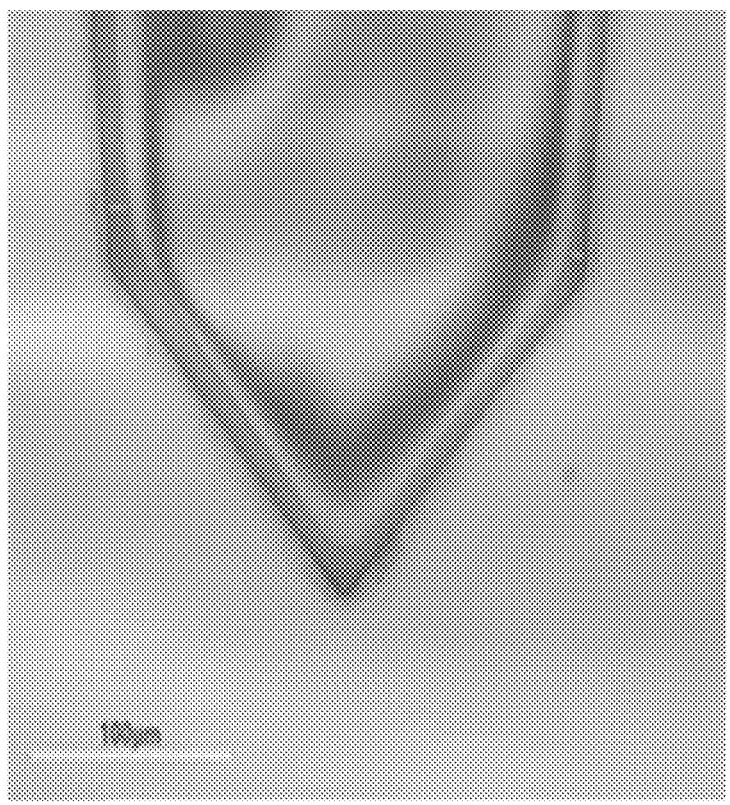
FIG. 6C illustrates another portion of the probe shown in FIG. 6A.

FIGS. 6A to 6C illustrate a thin film encapsulation layer of a probe manufactured through the thin film encapsulation layer formation shown in FIG. 5.

The thin film encapsulation layers 400-1 and 400-2 formed on the surface of the probe 200 are shown. The thin film encapsulation layers 400-1 and 400-2 may efficiently protect the OLED integrated into the probe shank 310 from the external environment.

Figure 7:
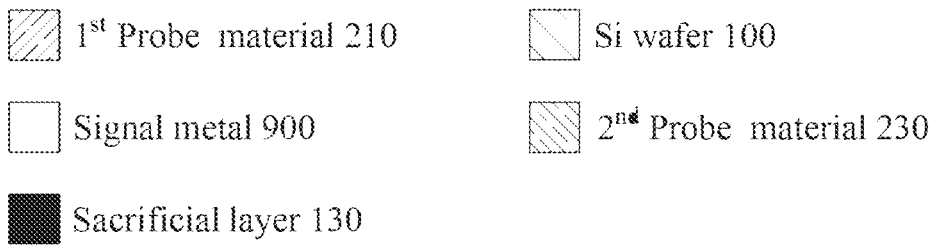
FIG. 7 illustrates an example of a process of manufacturing a probe.
Figure 7:
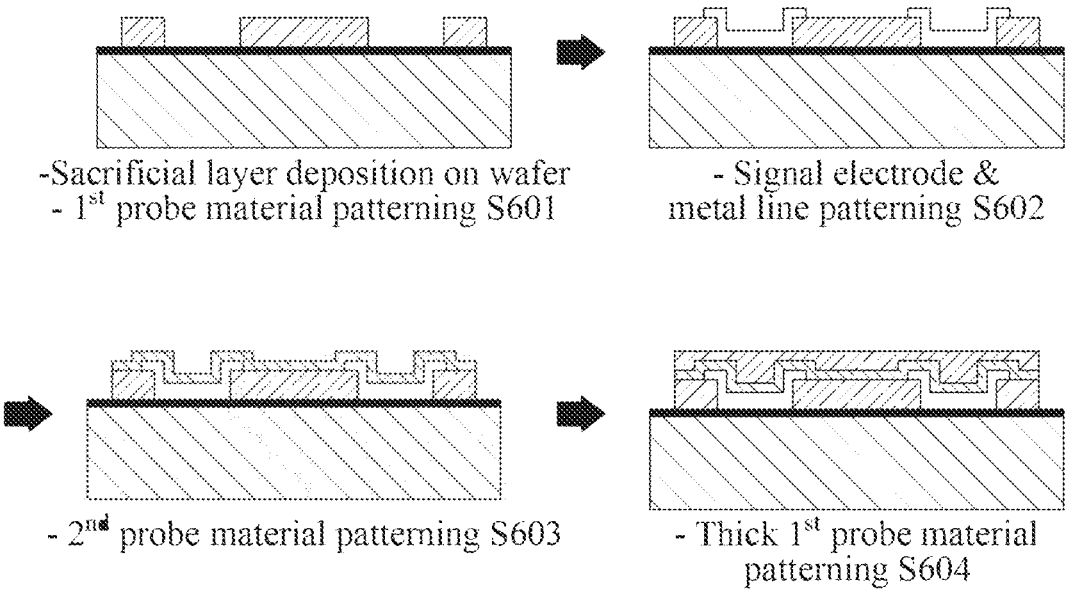

FIG. 7 illustrates an example of a process of manufacturing a probe.

The probe 200 may be manufactured on the wafer 100. For example, the probe 200 may be manufactured by depositing the first probe material 210, the second probe material 230, and a signaling electrode 900 on the wafer 100.

In operation S601, the sacrificial layer 130 may be deposited on the wafer 100, and the first probe material 210 may be patterned on the sacrificial layer 130. By depositing the sacrificial layer 130 on the wafer 100, the probe 200 that is manufactured may be separated from the wafer. An insulator may be used as the first probe material 210 to form the structure of the probe 200.

In operation S602, the signaling electrode 900 and/or the metal contact line may be patterned. For example, the signaling electrode 900 and/or the metal contact line may be patterned by depositing a metal layer on a fine pattern of the photoresist 500 and then lifting off the photoresist 500.

In operation S603, the second probe material 230 may be patterned on the top and the outside of the first probe material 210, the signaling electrode 900, and/or the metal contact line. The second probe material 230 may improve adhesion by using a material different from the first probe material 210. Since the second probe material 230 is deposited on the entire surface of the wafer, the photoresist 500 and a metal mask may be used to form the second probe material 230 at the bottom to enclose a region in which the first probe material 230, the signaling electrode 900, and the metal contact line are deposited.

In operation S604, the first probe material 210 may be patterned on the second probe material 230. For example, the first probe material 210 may be patterned using the photoresist 500 and the metal mask.

For example, the photoresist 500 may be patterned on the second probe material 230, and a metal layer may be deposited on the photoresist 500. In order to etch the second probe material 230 deposited on an unnecessary region, the metal mask may be patterned to fit a required region. The photoresist 500 may be patterned only in a region for etching the second probe material 230 and may be lifted off together with the metal layer. In this case, the metal mask may be Al.

The second probe material 230 may be etched except for the region blocked by the metal mask. For example, the second probe shank material 230 in an unnecessary region may be etched through $O_2$ plasma etching.

The metal mask deposited to etch the second probe material 230 may be removed. After that, the first probe material 210 may be patterned on the very top. For example, the first probe material 210 may be formed thickly on the underlying layers.

Figure 8A:
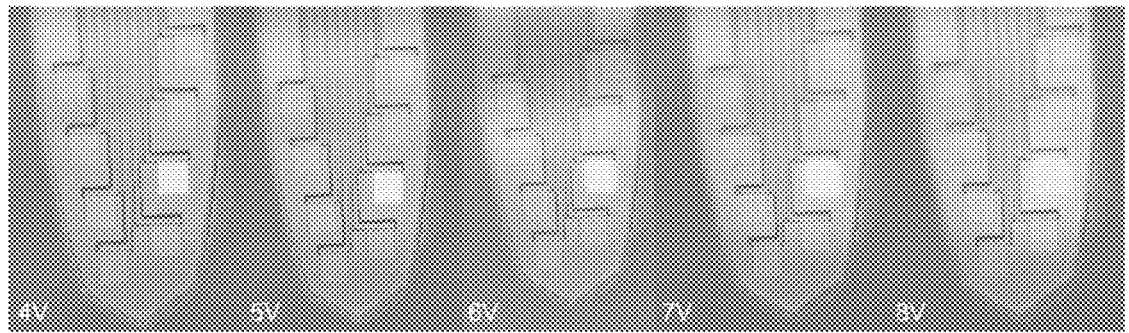
FIG. 8A illustrates light emission of a probe manufactured by the organic light source integration method shown in FIG. 1.
Figure 8B:
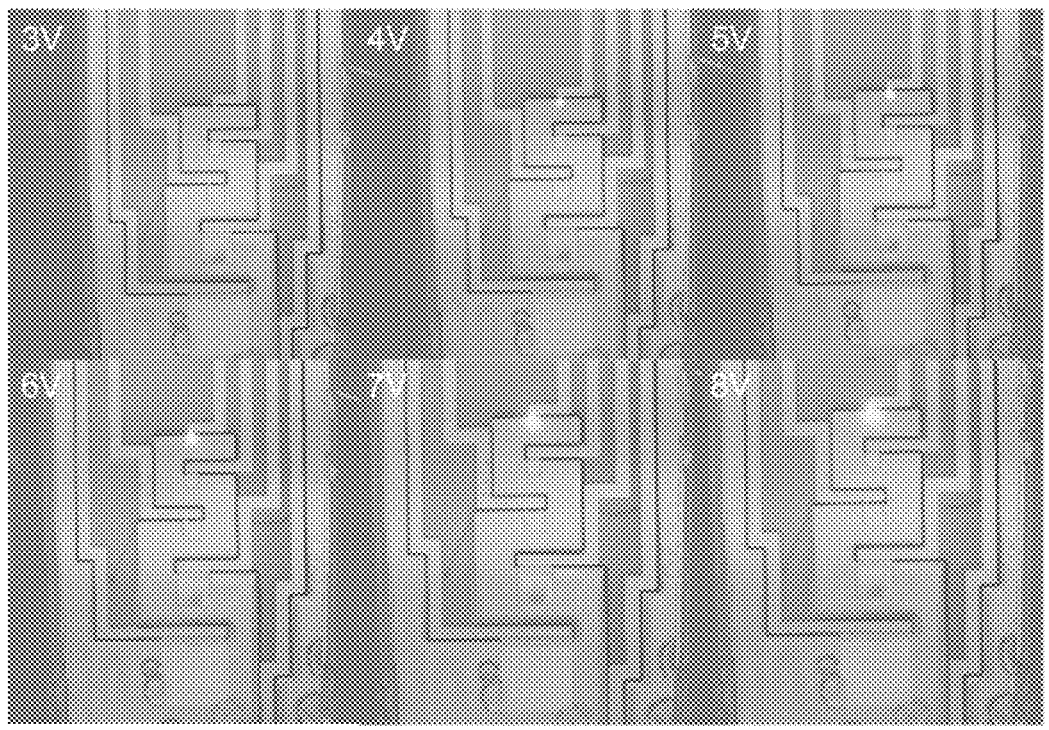
FIG. 8B illustrates light emission of a probe manufactured by the organic light source integration method shown in FIG. 1.

FIGS. 8A and 8B illustrate light emission of a probe manufactured by the organic light source integration method shown in FIG. 1, and FIGS. 8C to 8E are graphs showing the performance of a probe manufactured by the organic light source integration method shown in FIG. 1.

Referring to FIGS. 8A to 8B, it may be learned that an organic light source is successfully integrated into the probe shank 310 and emits light.

Figure 8C:
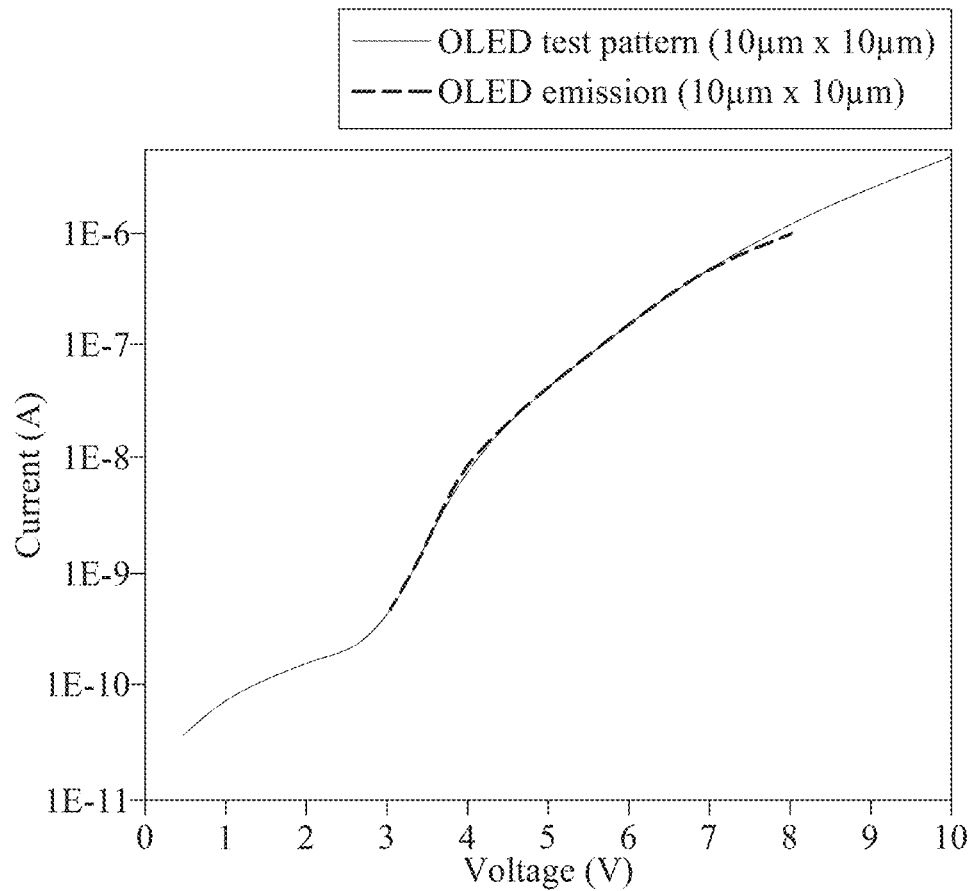
FIG. 8C is a first graph showing the performance of a probe manufactured by the organic light source integration method shown in FIG. 1.
Figure 8D:
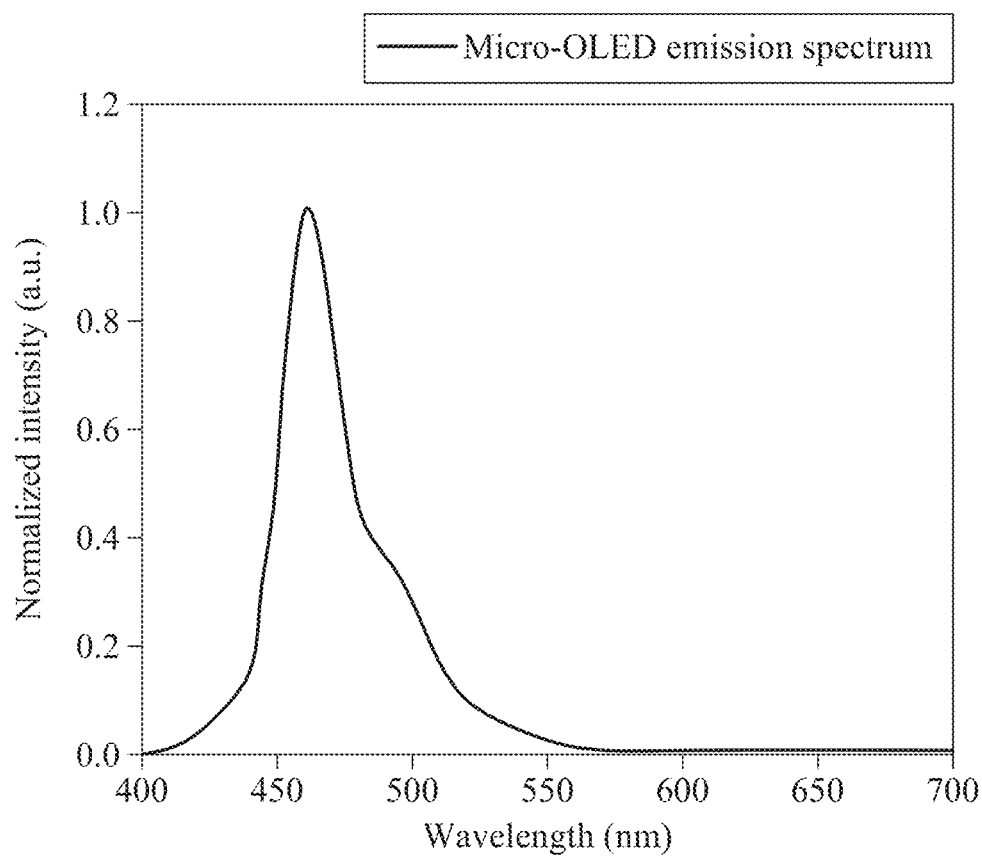
FIG. 8D is a second graph showing the performance of a probe manufactured by the organic light source integration method shown in FIG. 1.
Figure 8E:
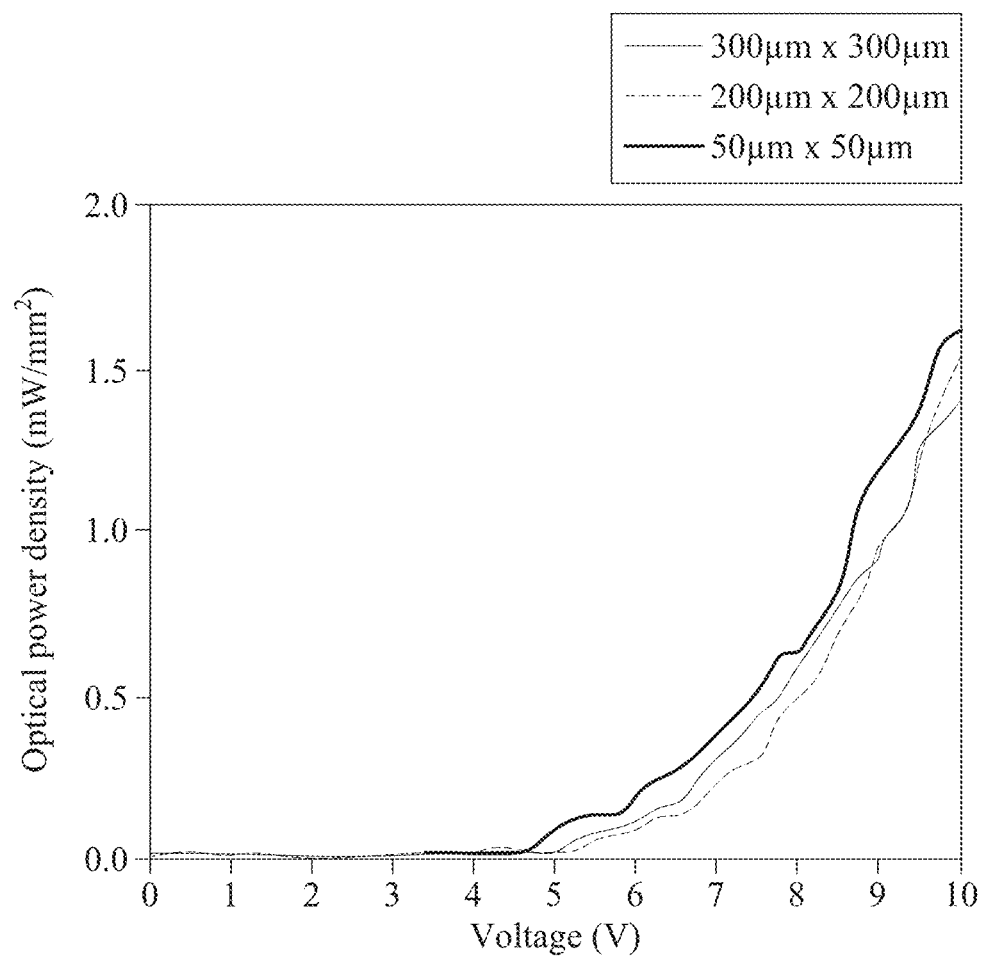
FIG. 8E is a third graph showing the performance of a probe manufactured by the organic light source integration method shown in FIG. 1.

FIG. 8C shows I-V data of the organic light source. Each of the FIGS. 8D and 8E shows wavelength spectrum data and optical power density data of the organic light source. The wavelength should be between 450 nm and 470 nm and the optical power density should be at least 1 $mW/mm^2$, which shows that both are satisfied.

By manufacturing the organic light source in micro size through fine patterning of the anode 300-1, and by integrating the micro-sized organic light source that may stably operate from the external environment through fine patterning of the thin film encapsulation layers 400-1 and 400-2 into the brain probe 200, local photic stimulation on neurons and neural signal measurement therethrough may be enabled.

In addition, since the light emitting layer of the micro-OLED is manufactured by thermal evaporation using a shadow mask, OLED pixels deposited on the brain probe 200 may be manufactured in various colors through shadow mask patterning. In other words, even a single brain probe 200 may irradiate light of various wavelengths and thereby stimulate various photoproteins, and thus more types of neurons may be activated at a time.

The patterning process of the thin film encapsulation layers may independently protect each OLED pixel in a device such as an OLED microarray in the future.

The data measured by the device manufactured according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher-level code that may be executed by the computer using an interpreter. The above-described devices may be configured to act as one or more software modules in order to perform the operations of the above-described example embodiments, or vice versa.

The software may include a computer program, a piece of code, an instruction, or some combination thereof, to independently or uniformly instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network-coupled computer systems so that the software is stored and executed in a distributed fashion. The software and data may be stored by one or more non-transitory computer-readable recording mediums.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

What is claimed is:

1. A method of integrating an organic light source, the method comprising:
    forming a first thin film encapsulation layer on a probe shank;
    depositing a first electrode in a first region on the first thin film encapsulation layer;
    depositing an insulating layer in a second region on the first thin film encapsulation layer, wherein the insulating layer includes an insulating material;
    depositing a light emitting layer on the first electrode and the insulating layer;
    depositing a second electrode on the light emitting layer; and
    forming a second thin film encapsulation layer on the second electrode;
    wherein the forming of the first thin film encapsulation layer comprises:
        patterning a photoresist in a region on a wafer except for the probe shank to form the first thin film encapsulation layer on the probe shank;
        coating an entire surface of the wafer with a thin film encapsulation layer; and
        forming the first thin film encapsulation layer by performing lift-off on the thin film encapsulation layer.

2. The method of claim 1, wherein the light emitting layer comprises an organic light emitting material.

3. The method of claim 1, wherein the depositing of the first electrode comprises:
    forming a fine pattern on the first thin film encapsulation layer using a photoresist;
    depositing a metal layer on the fine pattern; and
    forming the first electrode in the first region by performing lift-off on the metal layer.

4. The method of claim 3, wherein the forming of the fine pattern comprises patterning a region using the photoresist, except for a region for the first electrode and a region in which the first electrode is to be coupled to a power supply.

5. The method of claim 1, wherein the depositing of the insulating layer comprises depositing the insulating layer only in the second region so that only a region for the first electrode is opened on the first thin film encapsulation layer.

6. The method of claim 1, wherein the depositing of the light emitting layer comprises depositing the light emitting layer in high vacuum using a thermal evaporator.

7. The method of claim 1, wherein the depositing of the light emitting layer comprises depositing the light emitting layer only on the first electrode without covering a contact line of the second electrode.

8. The method of claim 1, wherein the coating of the entire surface of the wafer with the thin film encapsulation layer comprises coating the entire surface of the wafer with the thin film encapsulation layer through atomic layer deposition (ALD) and spin coating.

9. A method of integrating an organic light source, the method comprising:
    forming a first thin film encapsulation layer on a probe shank;
    depositing a first electrode in a first region on the first thin film encapsulation layer;
    depositing an insulating layer in a second region on the first thin film encapsulation layer, wherein the insulating layer includes an insulating material;
    depositing a light emitting layer on the first electrode and the insulating layer;
    depositing a second electrode on the light emitting layer; and
    forming a second thin film encapsulation layer on the second electrode;
    wherein the forming of the second thin film encapsulation layer comprises:
        patterning a photoresist in a region on a wafer except for the probe shank to form the second thin film encapsulation layer on the second electrode;
        coating an entire surface of the wafer with a thin film encapsulation layer; and
        forming the second thin film encapsulation layer by performing lift-off on the thin film encapsulation layer.

10. A method of integrating an organic light source, the method comprising:
    forming a first thin film encapsulation layer on a probe shank;
    depositing a first electrode in a first region on the first thin film encapsulation layer;
    depositing an insulating layer in a second region on the first thin film encapsulation layer, wherein the insulating layer includes an insulating material;
    depositing a light emitting layer on the first electrode and the insulating layer;
    depositing a second electrode on the light emitting layer;
    forming a second thin film encapsulation layer on the second electrode;
    depositing a sacrificial layer on a wafer; and
    manufacturing the probe shank on the sacrificial layer.

11. The method of claim 1, wherein the probe shank comprises a signaling electrode.

* * * * *